uscript010664531B2

(12) United States Patent
Phan et al.

(10) Patent No.: US 10,664,531 B2
(45) Date of Patent: May 26, 2020

(54) PEER-BASED USER EVALUATION FROM MULTIPLE DATA SOURCES

(71) Applicant: Samsung Electronics Co., Ltd., Suwon-si, Gyeonggi-do (KR)

(72) Inventors: Thomas Phan, San Jose, CA (US); Changha Lim, Hayward, CA (US)

(73) Assignee: Samsung Electronics Co., Ltd., Suwon-si (KR)

(*) Notice: Subject to any disclaimer, the term of this patent is extended or adjusted under 35 U.S.C. 154(b) by 205 days.

(21) Appl. No.: 15/406,554

(22) Filed: Jan. 13, 2017

(65) Prior Publication Data

US 2018/0203926 A1 Jul. 19, 2018

(51) Int. Cl.

| G06F 7/00 | (2006.01) |
| G06F 16/951 | (2019.01) |
| G16H 50/70 | (2018.01) |
| G06Q 10/10 | (2012.01) |
| G16H 20/30 | (2018.01) |
| G06Q 30/06 | (2012.01) |
| G06Q 30/02 | (2012.01) |
| G16H 20/10 | (2018.01) |
| G16H 20/70 | (2018.01) |
| G16H 10/60 | (2018.01) |

(Continued)

(52) U.S. Cl.
CPC .......... *G06F 16/951* (2019.01); *G06Q 10/10* (2013.01); *G06Q 30/02* (2013.01); *G06Q 30/06* (2013.01); *G16H 10/60* (2018.01); *G16H 20/10* (2018.01); *G16H 20/30* (2018.01); *G16H 20/70* (2018.01); *G16H 50/70* (2018.01); *H04L 43/10* (2013.01); *H04L 67/22* (2013.01)

(58) Field of Classification Search
CPC . G06F 17/30864; G06F 16/951; H04L 43/10; H04L 63/1433; G16H 20/10
USPC ................................ 707/758, 769, 827, 622
See application file for complete search history.

(56) References Cited

U.S. PATENT DOCUMENTS

| 8,386,914 B2 | 2/2013 | Baluja et al. |
| 8,781,882 B1 | 7/2014 | Arboletti et al. |
| 8,825,618 B2 | 9/2014 | Martin et al. |

(Continued)

FOREIGN PATENT DOCUMENTS

| KR | 10-20070117756 A | 12/2007 |
| KR | 10-20100071869 A | 6/2010 |

(Continued)

OTHER PUBLICATIONS

International Search Report and Written Opinion dated Apr. 18, 2018 for International Application PCT/KR2018/000697 from Korean Intellectual Property Office, pp. 1-9, Republic of Korea.

(Continued)

*Primary Examiner* — Md I Uddin
(74) *Attorney, Agent, or Firm* — Sherman IP LLP; Kenneth L. Sherman; Steven Laut

(57) ABSTRACT

A method of user evaluations includes transforming data from different data sources to preserve privacy of the data. The group of similar peers is created based on the data from the different data sources. The group of similar peers is optimized by selecting a combination of transformed data from the different data sources. An evaluation for a user against the group of similar peers is dynamically performed based on evaluation metrics. The evaluation is provided to an electronic device.

18 Claims, 12 Drawing Sheets

(51) Int. Cl.
*H04L 12/26* (2006.01)
*H04L 29/08* (2006.01)

(56) References Cited

U.S. PATENT DOCUMENTS

| | | |
|---|---|---|
| 8,832,262 B2 | 9/2014 | Hamilton et al. |
| 8,998,830 B2 | 4/2015 | Halperin et al. |
| 9,262,551 B2 | 2/2016 | Wilson et al. |
| 9,329,212 B2 | 5/2016 | Benes et al. |
| 9,384,493 B2 | 7/2016 | Harris et al. |
| 9,461,890 B1 | 10/2016 | Nair et al. |
| 9,461,992 B2 | 10/2016 | Outwater et al. |
| 2005/0086300 A1* | 4/2005 | Yeager .................. G06F 9/544 709/204 |
| 2007/0016528 A1 | 1/2007 | Verhaegh et al. |
| 2007/0150515 A1* | 6/2007 | Brave ............... G06F 17/30867 |
| 2009/0201176 A1 | 8/2009 | Takanori et al. |
| 2012/0191757 A1 | 7/2012 | Gross et al. |
| 2013/0226967 A1 | 6/2013 | Gross et al. |
| 2013/0254680 A1* | 9/2013 | Buhr ...................... A63F 13/12 715/753 |
| 2014/0089003 A1 | 3/2014 | Frey et al. |
| 2014/0125480 A1 | 5/2014 | Utter |
| 2014/0142905 A1 | 5/2014 | Drees et al. |
| 2016/0078377 A1 | 3/2016 | Chapman |
| 2016/0182556 A1* | 6/2016 | Tatourian ............... G06F 21/554 726/25 |
| 2019/0208114 A1* | 7/2019 | Ginat ....................... G06K 9/00 |

FOREIGN PATENT DOCUMENTS

| | | |
|---|---|---|
| WO | 2011153425 A2 | 12/2011 |
| WO | 2016186327 A1 | 11/2016 |

OTHER PUBLICATIONS

Extended European Search Report dated Nov. 26, 2019 for European Application No. 18739397.0 from European Patent Office, pp. 1-8, Munich, Germany.

\* cited by examiner

PEER-BASED USER EVALUATION FROM MULTIPLE DATA SOURCES

TECHNICAL FIELD

One or more embodiments relate generally to automatic user evaluations, and in particular, to improving user evaluations by automatically performing user evaluations in view of similar peer groups based on multiple connected devices and multiple institutions.

BACKGROUND

A standard and often crucial procedure for many users is to have their effort or condition judged formally by an evaluator. An evaluator assesses the user (or an item belonging to or produced by the user) on one or more evaluation metrics, where the final assessment may affect the user in some tangible manner. Importantly, such opportunities for evaluation may occur only once or a few times in a calendar year because the evaluator and/or the user does not have the time or resources to continuously have the evaluation performed.

SUMMARY

One or more embodiments relate to automatically performing user evaluations in view of similar peer groups based on multiple connected devices and multiple institutions. In some embodiments, a method of evaluations includes transforming data from different data sources to preserve privacy of the data. The group of similar peers is created based on the data from the different data sources. The group of similar peers is optimized by selecting a combination of transformed data from the different data sources. An evaluation for a user against the group of similar peers is dynamically performed based on evaluation metrics. The evaluation is provided to an electronic device.

In some embodiments, an electronic device includes a memory configured to store instructions. At least one processor is configured to execute the instructions to: transform data from different data sources to preserve privacy of the data, create a group of similar peers based on the data from the different data sources, optimize the group of similar peers by selection of a combination of transformed data from the different data sources, dynamically perform an evaluation for a user against the group of similar peers based on evaluation metrics, and provide the evaluation to a display of the electronic device.

In some embodiments, a non-transitory processor-readable medium that includes a program that when executed by a processor performs a method. The method comprises transforming data from different data sources to preserve privacy of the data. The processor creates a group of similar peers based on the data from the different data sources. The group of similar peers is optimized by selecting a combination of transformed data from the different data sources. An evaluation for a user is dynamically performed against the group of similar peers based on evaluation metrics. The evaluation is provided to an electronic device.

These and other features, aspects and advantages of the one or more embodiments will become understood with reference to the following description, appended claims and accompanying figures.

DETAILED DESCRIPTION

Figure 1:
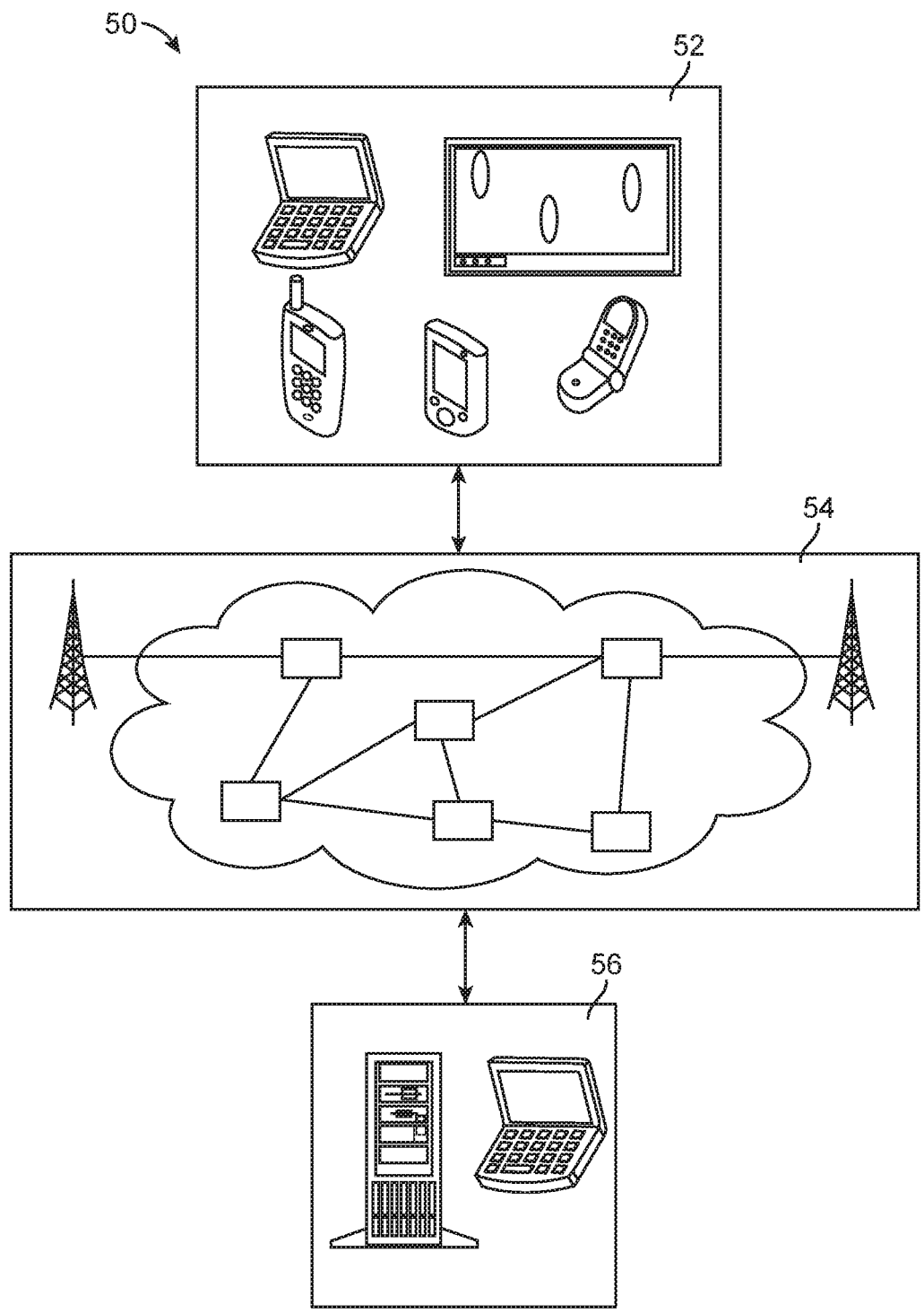
FIG. 1 shows an electronic system for automatically performing user evaluations in view of similar peer groups based on multiple connected devices and multiple institutions, according to some embodiments.

The following description is made for the purpose of illustrating the general principles of one or more embodiments and is not meant to limit the inventive concepts claimed herein. Further, particular features described herein can be used in combination with other described features in each of the various possible combinations and permutations. Unless otherwise specifically defined herein, all terms are to be given their broadest possible interpretation including meanings implied from the specification as well as meanings understood by those skilled in the art and/or as defined in dictionaries, treatises, etc.

One or more embodiments provide for automatically performing user evaluations in view of similar peer groups based on multiple connected devices and multiple institutions. In some embodiments, a method of user evaluations includes transforming data from different data sources to preserve privacy of the data. The group of similar peers is created based on the data from the different data sources. The group of similar peers is optimized by selecting a combination of transformed data from the different data sources. An evaluation for a user against the group of similar peers is dynamically performed based on evaluation metrics. The evaluation is provided to an electronic device.

Evaluations of users occur in many situations. The following are several examples of user evaluations. A physician may evaluate a patient once a year for a check-up to see if the latter is meeting health goals. In this case, evaluation metrics can include exercise frequency or rehabilitation progress, and the outcome may be a change in medication or other therapy. A manager may evaluate an employee twice a year to see if the latter is meeting performance goals. Evaluation metrics can include overall productivity as measured by tasks completed and sales generated, and the outcome can be an increase or decrease in wage. A professor may evaluate a student at the end of a semester to see if the latter is meeting expected learning outcomes. Evaluation metrics can include number of instructional exercises passed and average test score, and the outcome can be a passing or failing grade. An automobile mechanic may evaluate a user's car during an annual tuneup to see if the latter is operating efficiently and safely. Evaluation metrics can include number of failed physical parts and manifested oil leaks, and the outcome can be a replacement of engine parts.

The critical aspect of conventional assessments is that the evaluator can only formally perform the judgment a few discrete times during a calendar year. Reasons may include, but are not limited to: the evaluator has too many subjects to evaluate; having the assessment procedure performed multiple times is prohibitively costly in time and/or money for the user; or there are only a few available times when the assessment procedure can be performed due to institutional requirements or norms.

One or more embodiments provide a benefit for the user by performing assessments continuously throughout the year on a real-time basis so that the user can have an understanding of his or her status in preparation for a formal assessment that may be provided at a much later time. One example result would be that the one or more embodiments provide for the user to make sure that desired metrics and goals have been, or are in the process of, being met before a formal assessment with the evaluator. Some of the beneficial features of the one or more embodiments are that they provide the user with vital ongoing evaluation even if formal assessment is not available, they compare the user with improved peer grouping, they provide for improved clustering with comprehensive features from multiple institutions and multiple connected devices, they provide for improved user characterization from comprehensive features (versus features from only one institution) and feature weighting based on evaluation domain, they provide for data transformation to preserve privacy of the data, and the frequency of evaluation is adaptive to context and evaluation results.

FIG. 1 shows an electronic system 50 that may be employed with one or more embodiments. The electronic system 50 includes a first device 52, such as a client or a server, connected to a second device 56, such as a client or server. The first device 52 may communicate with the second device 56 with a communication path 54, such as a wireless or wired network.

In some examples, the first device 52 may be of any of a variety of networked devices. The first device 52 may couple directly or indirectly to the communication path 54 to communicate with the second device 56 or may be a stand-alone device.

For illustrative purposes, the display system 50 is described with the first device 52 as a display device, although it is understood that the first device 52 may be a variety of different types of devices. For example, the first device 52 may also be a device for presenting images or a multi-media presentation. A multi-media presentation may be a presentation including sound, a sequence of streaming images or a video feed, or a combination thereof. As an example, the first device 52 may be a ultra-high definition TV (UHDTV), or any other type of UD display device (e.g., monitor, video panel, heads up display (HUD), smart telephone, tablet device, video device, kiosk, gaming device, etc.).

The second device 56 may be any of a variety of centralized or decentralized computing devices, image or video transmission devices. For example, the second device 56 may be a smart TV, a multimedia computer, a tablet, a laptop computer, a desktop computer, a video game console, grid-computing resources, a virtualized computer resource, cloud computing resource, routers, switches, peer-to-peer distributed computing devices, a media playback device, a Digital Video Disk (DVD) player, a three-dimension enabled DVD player, a recording device, such as a camera or video camera, or a combination thereof. In another example, the second device 56 may be a signal receiver for receiving broadcast or live stream signals, such as a television receiver, a cable box, a satellite dish receiver, or a web enabled device.

The second device 56 may be centralized in a single room, distributed across different rooms, distributed across different geographical locations, embedded within a telecommunications network, etc. The second device 56 may have a means for coupling with the communication path 54 to communicate with the first device 52.

For illustrative purposes, the electronic system 50 is described with the second device 56 as a computing device, although it is understood that the second device 56 may be different types of devices. Also for illustrative purposes, the display system 50 is shown with the second device 56 and the first device 52 as end points of the communication path 54, although it is understood that the display system 50 may have a different partition between the first device 52, the second device 56, and the communication path 54. For example, the first device 52, the second device 56, or a combination thereof may also function as part of the communication path 54.

The communication path 54 may be a variety of networks. For example, the communication path 54 may include wireless communication, wired communication, optical, ultrasonic, or the combination thereof. Satellite communication, cellular communication, BLUETOOTH®, Infrared Data Association standard (IrDA), wireless fidelity (WiFi), and worldwide interoperability for microwave access (WiMAX) are examples of wireless communication that may be included in the communication path 54. Ethernet, digital subscriber line (DSL), fiber to the home (FTTH), high-definition multimedia interface (HDMI) cable, and plain old telephone service (POTS) are examples of wired communication that may be included in the communication path 54.

Further, the communication path 54 may traverse a number of network topologies and distances. For example, the communication path 54 may include direct connection, personal area network (PAN), local area network (LAN), metropolitan area network (MAN), wide area network (WAN), a combination thereof, etc.

One or more embodiments may provide processing for automatically evaluating a user against a group of similar peers by comparing evaluation metrics. The group of similar peers is created based on data from multiple connected devices and from multiple online institutions, where a transformation process preserves the privacy of online data sources and the data collection is customized for the application and the data sources. The comprehensive combination of data from these multiple sources, feature weighting, and outlier removal additionally help produce better peer groups. The frequency of the evaluation is dynamically adaptable and may vary based on both context and the result of the evaluation.

In one or more embodiments, a user's peers may be found by applying clustering to find the closest other users according to distance (e.g., data distance, deviation, etc.) as measured with data coming from multiple connected devices (e.g., smart phones, computers, smart devices, tablet computing devices, etc.) and multiple online institutions. Each institution maintains its own private data, and to preserve this privacy, each institution may apply a transformation to convert raw numeric or categorical data to unidentifiable numeric features. Data collection may be customized to match the application (e.g., a fitness application uses only fitness data, etc.) and device characteristics or limitations (e.g., retrieving data from a battery-limited device should occur less frequently). The combination of features from multiple devices and multiple online institutions additionally allows each user to be characterized more completely than would be possible if data came from only one device or only one online institution. Once the clusters are using these features, users in the same cluster are measured according to evaluation metrics, and a particular user is assessed according to his or her placement with respect to descriptive statistics for the entire group (e.g., the mean, median, and percentiles of each evaluation metric). The frequency of evaluation of the user with respect to the peer group may vary depending on the context and evaluation result, resulting in less frequent or more frequent evaluations as needed. One or more embodiments produce evaluations in a continuous, real-time manner. If the user falls within a low region (e.g., low performance percentile) of the entire group, then an alert and a recommended course of action can be generated and sent (e.g., messaging, email, text message, voice message, facsimile, etc.) to an electronic device (e.g., a smart phone, computing device, tablet device, smart device (e.g., a smart TV, a smart appliance, a wearable device, etc.), etc. for access by the user. The evaluation can further be used by the evaluator to make sure the user is on track for improvement either during the year or during the formal assessment.

Figure 2:
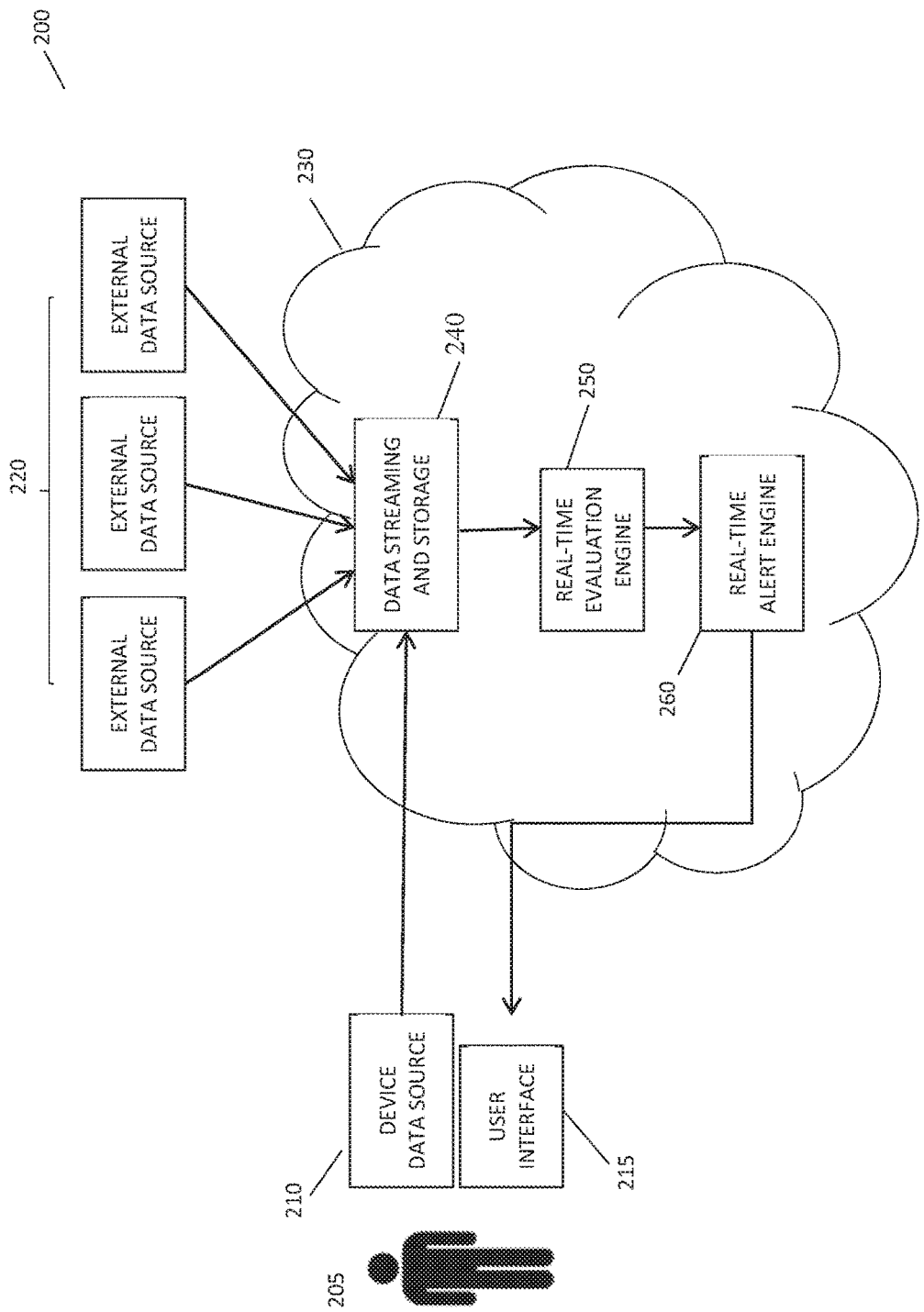
FIG. 2 shows an example architecture for automatically performing user evaluations in view of similar peer groups based on multiple connected devices and multiple institutions, according to some embodiments.

FIG. 2 shows an example architecture 200 for automatically performing user evaluations in view of similar peer groups based on multiple connected devices and multiple institutions, according to some embodiments. In one or more embodiments, the example architecture 200 includes an electronic device data source 210, a user interface 215, one or more external data sources 220, a cloud platform (or server) 230, data streaming and storage component 240, real-time evaluation engine 250, and a real-time alert engine 260. In one or more embodiments, a user 205 (or an item owned by or produced by the user 205) may require a formal assessment by an evaluator.

In the context of performance assessment, the user 205 (or an item owned or produced by the user 205) is required to undergo a formal assessment by an evaluator. For example, the user 205 may be: a medical patient who needs an annual checkup with a physician; an employee who is evaluated for job performance by a manager; a car owner who wants the car to be tuned up by a mechanic, etc. In each case, in the conventional evaluation the evaluator uses one or more pertinent evaluation metrics and determines the metrics for the user. Depending on the user's outcome with respect to the metrics, the evaluator takes some action. In the example with the physician and patient, the metrics may include average amount of exercise or the average peak heart rate achieved, and the outcome may be a change in prescribed medication or therapy. In these conventional scenarios, the assessment occurs only once or a few times a year because having continuous formal assessment is prohibitively expensive with respect to time or money. Nonetheless, it is important that the user continue to maintain high performance throughout the year. For example, for medical patients, it is important the user maintain good health and exercise, and for company employees, it is important that the user maintain high productivity. This year-round maintenance not only ensures an overall good condition for the user but also provides preparation for the formal assessment by the evaluator.

In one or more embodiments, to perform year-round assessment without an available evaluator, the architecture 200 assesses the user 205 by performing a comparison along multiple dimensions to similar peers in real-time. This comparison is described as follows. User features are obtained from multiple connected devices (e.g., multiple device data sources 210) and multiple online institution data sources (external data sources 220). In one or more embodiments, the multiple connected devices may include, but are not limited to: smartphones, wearable devices, IoT sensors, smart appliances, connected cars, medical devices, etc., and the multiple online institution data sources may include, but are not limited to, hospitals, police or law enforcement agencies, courts, web searches, social networks, etc.

In preparation for clustering of a user 205 (or multiple users 205 or user items) into peer groups, features may be formed from data obtained from the device data sources 210 (e.g., connected devices) and external data sources 220 (e.g., from multiple online services that are part of institutional organizations), where each feature corresponds to a particular measurable aspect. The institutions can identify the same person through a code, such as Social Security Number, etc. In some embodiments, one or more features may be the same as the assessment metrics used by an evaluator. For example, the user's exercise activity (e.g., obtained by a smart watch, smart phone or computing device connected to the smart watch, etc.) may be used both for clustering as well as for the assessment metric.

In one or more embodiments, the features for a user 205 may include but are not limited to: aspects from a hospital's medical records, such as age, height, weight, medical ailments, surgery history, medication history, medical test results, etc.; aspects from a consumer fitness wearable device or smartphone, such as number of steps walked, exercise duration, exercise intensity, exercise exertion, exercise type, resting heart rate, time in heart rate zones, etc.; aspects from survey answers, such as responses to questions regarding attitude toward health, sports, politics, etc.; aspects from a user's dietary journal, such as types of food eaten, calories consumed, frequency of meals, drinks, water consumption, etc.; aspects from a police criminal record, such as reports of fines, misdemeanors, felonies, jail time, etc.; aspects from geolocation tracking, such as places where the user exercises, time spent driving on the highway, places that the user frequents on the weekend, travel time, etc.; aspects from online behavior logging, such as activities on social networks or frequently visited websites; aspects from shopping, such as purchases made either online or at physical stores; aspects from demographic profiling, such as income, tax bracket, level of education, etc.; aspects from environmental Internet of Things (IoT) sensing, such as household temperature, home TV viewing habits, hours spent in the kitchen or other room, etc.; aspects from a connected car, such as percentage of time exceeding the speed limit, number of lane changes per minute, fuel use, etc.

In one or more embodiments, features for items owned by or produced by the user 205 can include but are not limited to: aspects related to the item components, such as the parts inside a car engine, etc.; aspects related to the provenance of the items, such as when and where car engine parts were purchased, etc.; aspects related to the behavior of the items, such as the average miles per gallon achieved by a car, etc. Because many of these aspects may come from different institutions, one or more embodiments may collect the data in a safe and trusted aggregation center, such as at the cloud platform (or server) 230. In one or more embodiments, the external data sources 220 provide data that is stored at the cloud platform (or server) 230 via the data streaming and storage component 240 (e.g., device or processing engine).

In one or more embodiments, institutions may have requirements to protect the privacy of the user 205, and thus the privacy of user data is maintained by each institution by application of its own transformation of the data that converts numeric or categorical data into a privacy-preserving alternative numeric or categorical representation. In one or more embodiments, each institution converts each aspect's raw data into a relative placement using descriptive statistics. For example, with respect to a user's weight, a hospital may replace an original value such as "220 lbs." with a relative value such as "61st percentile" over all users, or "1.5 standard deviations above the mean" over all users. In some embodiments, each institution may apply a one-way monotonic hashing algorithm that converts an original value into a different numerical value. One or more embodiments may replace the original name of the aspect with a random name; for example, an original aspect name of "weight" may be replaced by a new aspect name of "ABCD." Therefore, each institution's user aspects are protected within the bounds of the institution with the original data transformed into a privacy-preserving representation. These aspects then serve as the features used by clustering.

In one or more embodiments, the real-time alert engine 260 provides an evaluation result or assessment to the user interface 215. The user interface 215 may be a display on a mobile, wearable or fixed electronic device, delivered as a message or email, be delivered as audio (e.g., synthesized speech), faxed, etc.

Figure 5:
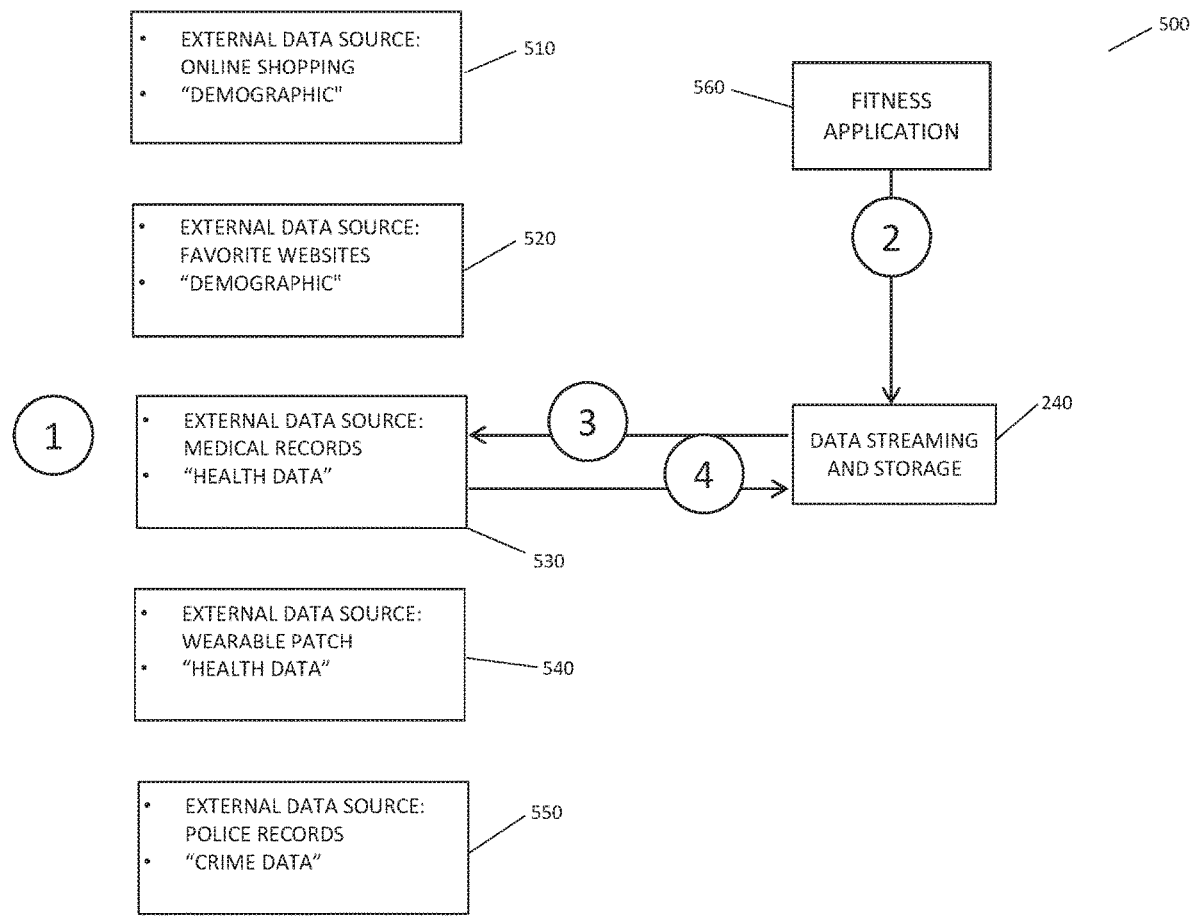
FIG. 5 shows an example of data customization for an application for automatically performing user evaluations in view of similar peer groups based on multiple connected devices and multiple institutions, according to an embodiment.

In one or more embodiments, data collection may be customized to match the needs of the application and improve the clustering process that occurs in the real-time evaluation engine 250 (see the example in FIG. 5). In one or more embodiments, each data source, whether a device data source 210 or online institution external data source 220, can identify its type of data or its type of features according to a predefined set of topics, such as "health," "demographics," "crime," etc. The application that desires the formation of user peer groups then identifies which topics are required to the data streaming and storage component 240. For example, a fitness application that produces groups of similar-health users may desire to retrieve data and data features that have been identified as a "health" type. Alternatively, the application may request "any" type of data. The data streaming and storage component 240 then retrieves the requested types of data.

In one or more embodiments, the user 205 may be evaluated by the architecture 200 in anticipation of, or in preparation for, a formal assessment performed by an evaluator. Users 205 are evaluated against related peers that are determined by using a distance calculated from data sources of multiple institutions and multiple connected devices using the real-time evaluation engine 250. The combination of features from multiple institutions and connected devices can be further transformed in order to characterize a user 205 more effectively than features from any single institution. The frequency of the evaluations dynamically changes based on context and prior evaluation results. If a user 205, for example, exhibits anomalously poor performance, an alert and recommended corrective action can be generated by the real-time alert engine 260 and sent to the user interface 215.

In one example, the user 205 is male, age 40-49, has a height of 180 cm, a weight of 79 kg, and averages 14,500 steps per day on Tuesday and Wednesday evenings (e.g., obtained from health records and a wearable device). This user 205 spends 3 hours per day on a social media platform (from social networking), has no criminal activity in the last 2 years (e.g., from police or court records), exceeds the driving speed limit 20% of the time (e.g., obtained from a connected car), and has a middle-class income (e.g., from online shopping and geolocation data). The real-time evaluation engine 250 processes the data and determines that the user 205 is in the $20^{th}$ percentile in physical activity among peers (e.g., found from a clustering based on all features). The real-time alert engine 260 generates and sends an alert that "The user is well below the median of his peers," and provides a recommendation of: "User should increase exercise on the weekend."

In another example, the user 205 is male, age 40-49, has a height of 180 cm, a weight of 79 kg, and averages 14,500 steps per day on Tuesday and Wednesday evenings (e.g., obtained from health records and a wearable device). This user 205 spends 3 hours per day on a social media platform (from social networking), has no criminal activity in the last 2 years (e.g., from police or court records), exceeds the driving speed limit 30% of the time (e.g., obtained from a connected car), and has a middle-class income (e.g., from online shopping and geolocation data). The real-time evaluation engine 250 processes the data and determines that the user 205 is in the $55^{th}$ percentile in physical activity among peers found from a clustering based on income level, neighborhood, and education level. The real-time alert engine 260 generates and sends an alert that "The user is near the median of his peers" and provides a recommendation of: "User is doing about average. Keep up current effort."

In another example, the user 205 is male, age 40-49, has a height of 180 cm, a weight of 79 kg, and averages 14,500 steps per day on Tuesday and Wednesday evenings (e.g., obtained from health records and a wearable device). This user 205 spends 3 hours per day on a social media platform (from social networking), has no criminal activity in the last 2 years (e.g., from police or court records), exceeds the driving speed limit 30% of the time (e.g., obtained from a connected car), and has a middle-class income (e.g., from online shopping and geolocation data). The real-time evaluation engine 250 processes the data and determines that the user 205 is in $80^{th}$ percentile in spending habits among peers found from a clustering based on aggressive driving style, online shopping, and police records. The real-time alert engine 260 generates and sends an alert that "The user is well above the median of his peers," and provides a recommendation of: "User is spending too much money. Reduce expenses."

One or more embodiments may include employing a distributed software architecture to store data and compute evaluations. In addition to the cloud platform or server 230 (e.g., a central secured server), one or more embodiments employ a set of secure servers, where user accounts are spread across a distributed system of servers.

Figure 3:
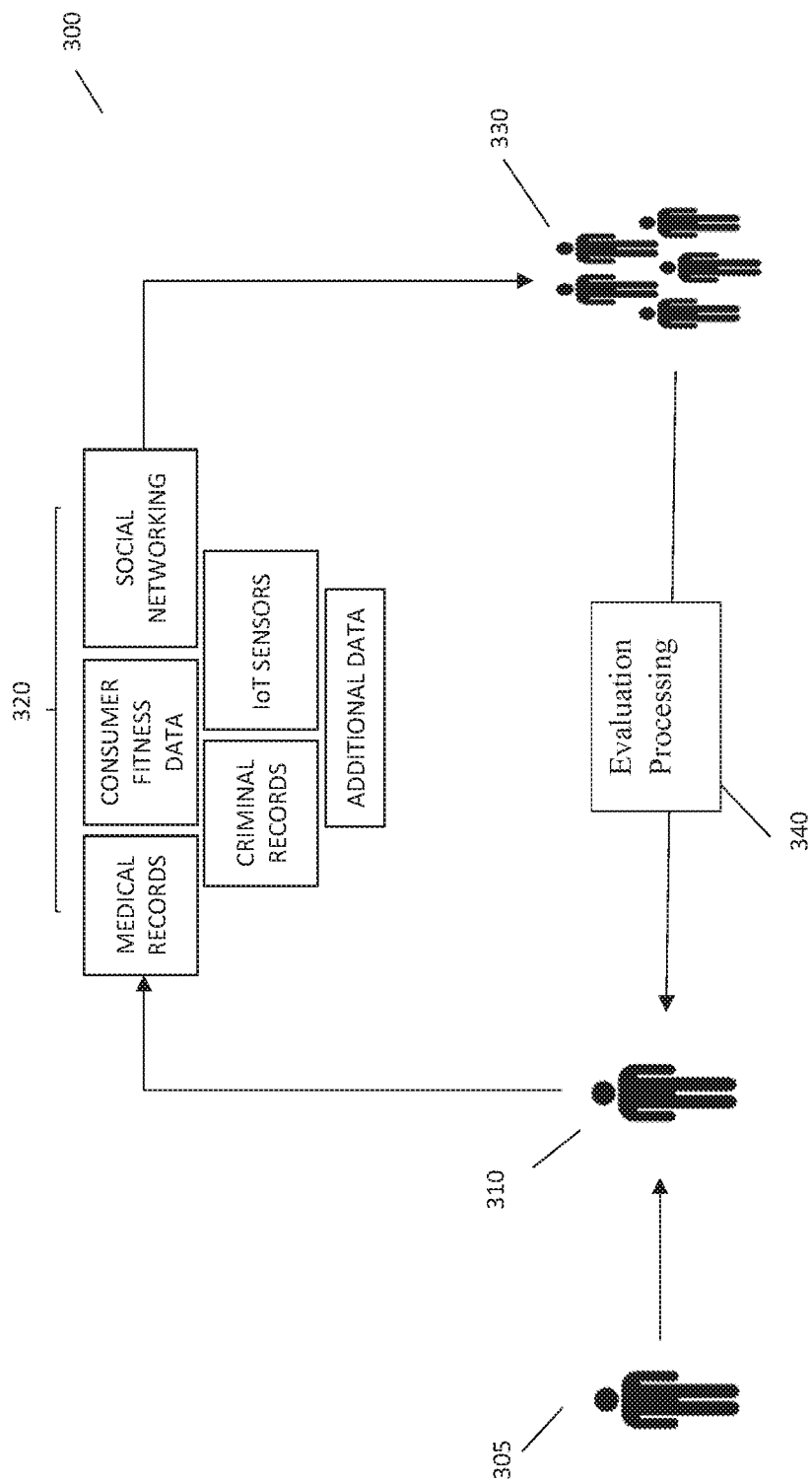
FIG. 3 shows an example flow diagram for automatically performing user evaluations in view of similar peer groups based on multiple connected devices and multiple institutions, according to an embodiment.

FIG. 3 shows an example flow diagram 300 for automatically performing user evaluations in view of similar peer groups based on multiple connected devices and multiple institutions, according to an embodiment. In the example 300, the authority 305 can only evaluate user 310 rarely (e.g., once a year). The architecture 200 (FIG. 2) characterizes user 310 by features from multiple data sources 320 (e.g., medical records, consumer fitness data, social networking data, criminal records, IoT sensors and any other additional data available. The architecture 200 creates cohort peers 330 that are similar to the user 310 by, for example, Euclidean distance. The evaluation processing 340 (e.g., using the real-time evaluation engine 250) evaluates the user 310 against the peer group 330 using descriptive statistics (e.g., percentiles) on a year-round basis using the evaluation metric(s) of: step count, calories consumed, surgery rehabilitation, work productivity. The user 310 then receives alerts and recommendations on a user interface 215 sent from the real-time alert engine 260. One or more embodiments may provide for using different similarity measurements to determine other users who are peers to a particular user. In addition to the Euclidean distance mentioned above, one or more embodiments employ a cosine similarity, Jaccard similarity, or Mahalanobis distance.

Figure 4:
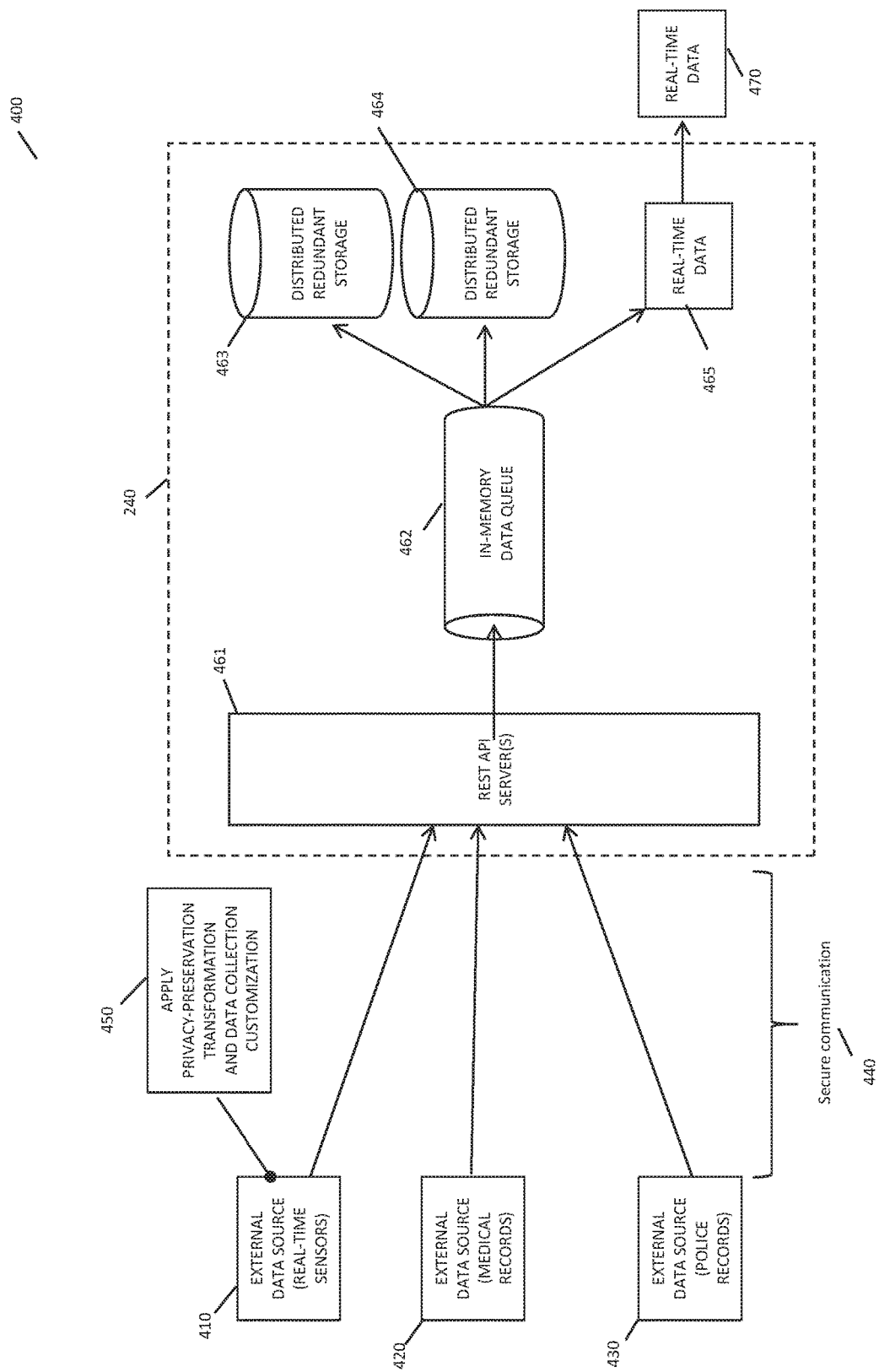
FIG. 4 shows data streaming and storage for automatically performing user evaluations in view of similar peer groups based on multiple connected devices and multiple institutions, according to an embodiment.

FIG. 4 shows data streaming and storage flow 400 for automatically performing user evaluations in view of similar peer groups based on multiple connected devices and multiple institutions, according to an embodiment. In one or more embodiments, the data streaming and storage component 240 includes one or more representational state transfer (REST) application programming interface (API) server 461, an in-memory queue 462, distributed redundant storage components 463 to 464 and real-time data component 465. The REST API server(s) 461 receives, queues, and stores data from multiple external data which may include, but are not limited to: external data source 410 (e.g., real-time sensors (e.g., data from consumer devices or other connected devices (e.g. smartphones, wearables, etc.)) and real-time sensor data from industrial devices (e.g., connected car(s), medical patch, IoT sensor network, etc.)), external data source 420 (e.g., medical records and physical attributes), external data source 430 (e.g., police/criminal, records). Additionally, external data sources may further include App usage from smartphone, etc. online activity from social networking, shopping, etc., geolocation from GPS tracking, among others.

In one or more embodiments, the data obtained from the external data sources (e.g., external data sources 410, 420 and 430) is transformed and/or customized at the data source (e.g., at 450). In one or more embodiments, the transformation converts the data to a privacy-preserving representation or number (e.g.: an original data value of 80 kg weight may be transformed to a relative value of 1 standard deviation from the mean; 2 felonies may be transformed to $95^{th}$ percentile in criminal activity). The transformation may include the application of a monotonic hashing function to the original data. The transformation may include replacing the original name of the data (e.g. "user weight") with a new name. Data collection may be customized for: the application requirements (e.g., medical application may acquire data only from health-related sources; monetary loan/credit application may acquire any data related to demographics), the data source's capabilities or limitations (e.g., a battery-powered sensor may acquire data less frequently to save power; a multi-sensor smartphone may acquire only the data relevant for an application).

In one or more embodiments, secure communication 440 is used to send or transmit the data to the system REST API server(s) 461. The resulting data is eventually sent to the real-time evaluation engine 250 (FIG. 2).

FIG. 5 shows an example 500 of data customization for an application (e.g., a fitness application 560) for automatically performing user evaluations in view of similar peer groups based on multiple connected devices and multiple institutions, according to an embodiment. In one or more embodiments, data collection is based on needs of the application. In the example 500, the external data sources include: online shopping 510 (e.g., a demographic type of data), favorite websites 520 (e.g., a demographic type of data), medical records 530 (e.g., a health type of data), wearable patch 540 (e.g., a health type of data) and police records 550 (e.g., a crime type of data). In the example 500, at process reference 1, the external data sources (e.g., external data sources 510, 520, 530, 540 and 550) identify their available data and features according to pre-defined types or categories, for example: "Demographic" "Health Data" "Crime Data," etc. At process reference 2, the application 560 identifies what kinds of data sources and features it wants, e.g. "Health data", "ANY," etc. At process reference 3, the data streaming and storage component 240 signals relevant data sources to provide information for data "push" (or query them for information for data "pull"). At process reference 4, the external data sources provide the data to the data streaming and storage component 240.

Figure 6:
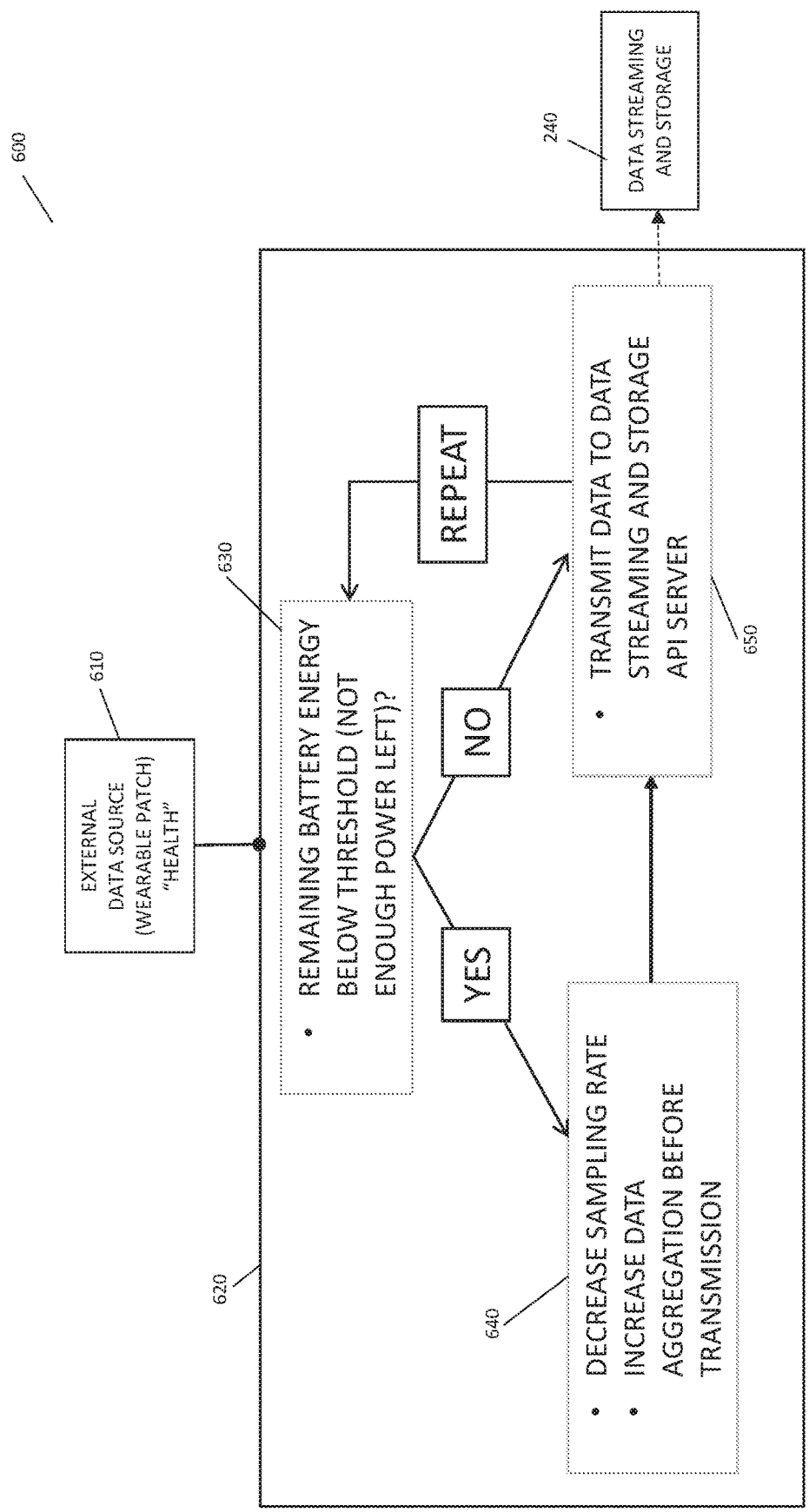
FIG. 6 shows an example of data customization for a data source for automatically performing user evaluations in view of similar peer groups based on multiple connected devices and multiple institutions, according to an embodiment.

FIG. 6 shows an example 600 of data customization for an external data source 610 for automatically performing user evaluations in view of similar peer groups based on multiple connected devices and multiple institutions, according to an embodiment. In example 600, the external data source 610 is a wearable patch that has "Health" type of data. In one or more embodiments, the external data source 610 includes a processing component 620 that performs the following. At block 630 it is determined whether remaining battery energy is below a threshold not (i.e., is there or is there not sufficient energy left for the wearable patch). If it is determined that the remaining battery energy is below a threshold, then the processing component proceeds to block 640 where the external data source decreases sampling rate, and/or increases data aggregation before transmission. Otherwise, the processing component 630 proceeds to block 650 where it transmits data to REST API server(s) 461 (FIG. 4).

Figure 7A:
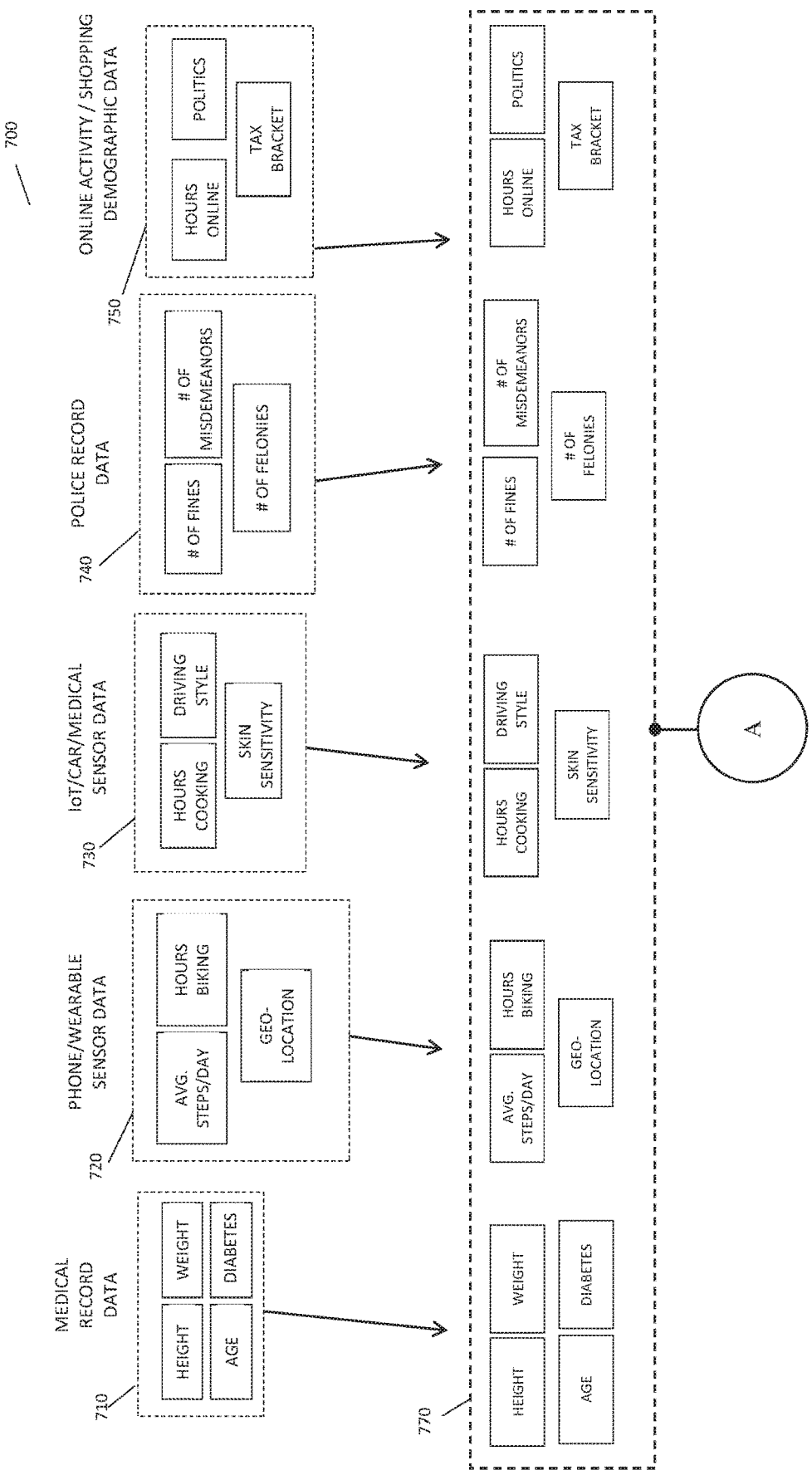
FIGS. 7A-B show an example of real-time evaluation engine for automatically performing user evaluations in view of similar peer groups based on multiple connected devices and multiple institutions, according to an embodiment.
Figure 7B:
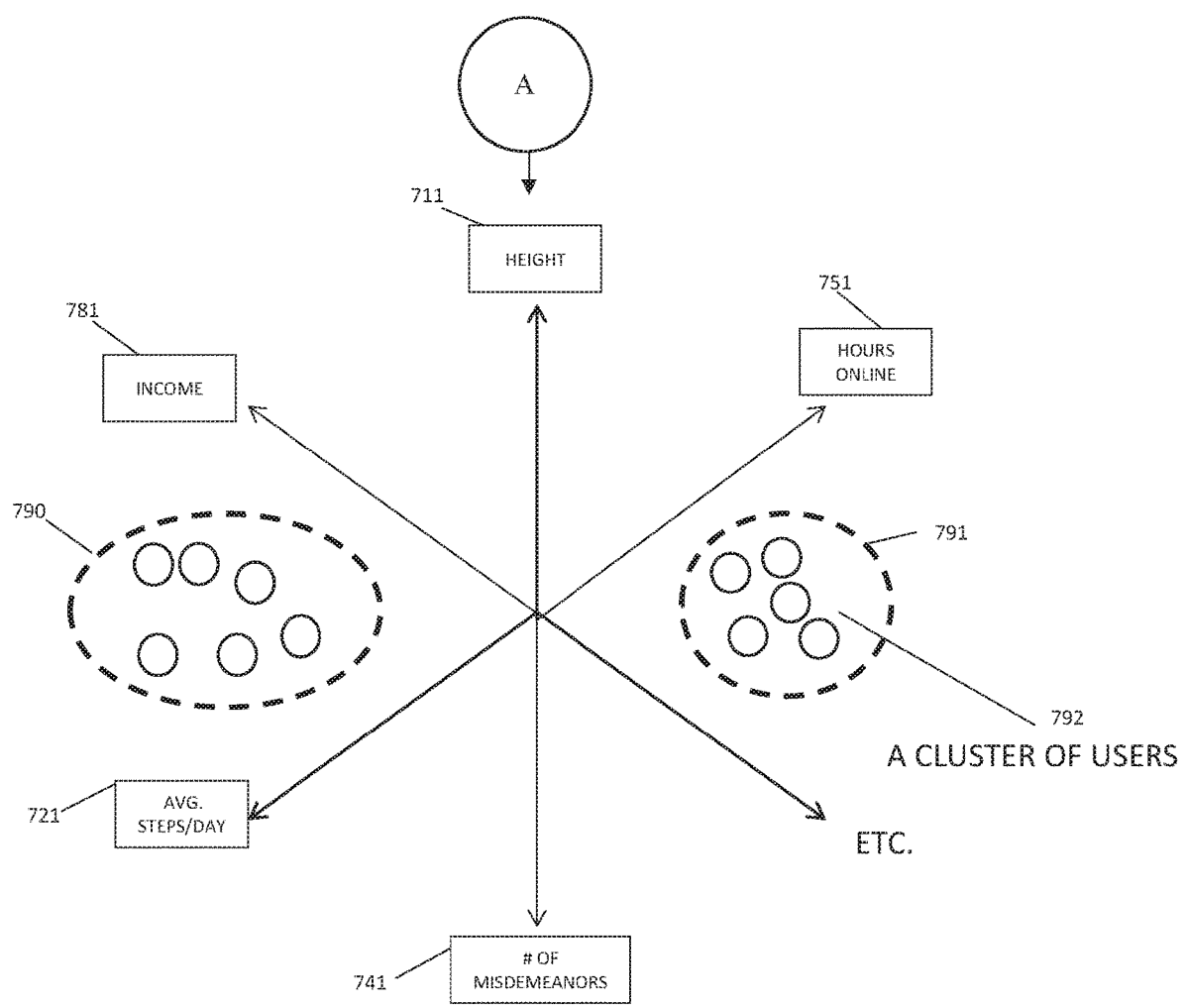

FIGS. 7A-B show an example 700 of the real-time evaluation engine 250 (FIG. 2) processing for automatically performing user evaluations in view of similar peer groups based on multiple connected devices and multiple institutions, according to an embodiment. In the example 700, the data from the external data sources include: medical record data 710 (e.g., height, weight, age, diabetes), phone/wearable sensor data 720 (e.g., average steps/day, hours biking, geo-location), IoT/Car/Medical sensor data 730 (e.g., hours cooking, driving style, skin sensitivity), police record data 740 (e.g., number of fines, number of misdemeanors, number of felonies) and online activity/shopping demographic data 750 (e.g., hours online, politics, tax bracket).

In one or more embodiments, the real-time evaluation engine 250 clusters the user (or an item owned by or produced by the user) with other similar peer users using features. Given the (transformed) features produced from the external data sources, the real-time evaluation engine 250 forms groups of related peers in order to facilitate the comparison of the user to similar users. The features from the multiple institutions are collected. In one or more embodiments, the REST API server(s) 461 (FIG. 4) assembles all the data features from the multiple data sources 710, 720, 730, 740, 750 into one list of features (a so-called feature vector 770) that characterize the user.

One or more embodiments may apply feature weighting to particular data features that are relevant to the application domain. For example, for a security application, only data from police record data may be relevant. The REST API server(s) 461 then applies a larger numeric weight to the data features that are obtained from a police record data source. Alternatively, a smaller numeric weight may be applied to non-related data features.

One or more embodiments may remove outlier user data. For example, if a particular user's data is well above the $99^{th}$ percentile of all user's data for number of steps walked or well below the $1^{st}$ percentile of all user's data, then that user may be removed prior to clustering. Including such outlier data would only serve to make the clusters more diffuse (that is, users in the same cluster be very unrelated when compared to clusters with outliers removed).

In one or more embodiments, another transformation may be applied to the feature vector 770 using a variety of known techniques. Principal component analysis (PCA) may be applied to transform the feature vector 770 of each user into a different space and keep a smaller number of features than in the original feature vector. In another embodiment, a feature selection process may be applied to the original feature vector 770 to again keep a smaller number of features.

In one or more embodiments, after these feature vector transformations, the features are treated as the representation of the user to a clustering process. By having features that come from multiple institutions, the one or more embodiments perform improved clustering as compared against clustering that is performed using only features from a single institution. One clustering result can be found to be quantitatively better than another clustering result by computing a metric on each cluster; such metrics may include sum-of-squared-error or a so-called silhouette coefficient.

Clustering processing may include but are not limited to the well-known k-Nearest Neighbor algorithm or the Agglomerative Clustering algorithm. Given all the users (each represented by a collection of features), the processing produces a list of clusters, where each cluster contains similar users. Similarity may be measured by the processing as the Euclidean distance between the feature vectors 770 of each user. As an example, one cluster may contain users who are under 25 years old, have diabetes, and exercise on the weekend. Another cluster may contain users who are over 45, have heart disease, and rarely exercise. Clustering is improved based on comprehensive features from multiple institutional sources and multiple connected devices, feature weighting, outlier user removal (e.g., remove clustered users with values beyond middle 98%), improvement is measured by lower SSE (sum of squared error) clustering metric, and a user is then evaluated with respect to peers via cluster statistics for some metric (e.g., step count; "User's step count is in the top 25% of similar users").

In one or more embodiments, descriptive statistics for the group are computed and each user is evaluated with respect to the group. With peer groups formed, descriptive statistics are computed and the user is appropriately placed relative to the group. For a given user's context and method of evaluation, one or more pertinent evaluation metrics are used by the evaluator. For each such metric, descriptive statistics are computed, such as the mean, median, standard deviation, quartiles, and deciles. The user's computed evaluation metric is then placed into a predetermined range. The evaluation metric must be retrieved from the institution that contains the data. In one embodiment, when the user data features are retrieved from an institution, the value of the evaluation metric must also be retrieved. For example, in a health context where the evaluation metric is the average duration of exercise per day, the user may be found to be above the 90th percentile within the group. This data can be retrieved from the health and fitness institution that owns this metric. In an employee evaluation context where the evaluation metric is the amount of sales completed, the user may be found to be one standard deviation below the mean. This data can be retrieved from a corporate institution that owns this metric. In a student evaluation context where the evaluation metric is the average score on exams, the user may be found to be below the 10th percentile. This data can be retrieved from the academic instructional that owns this metric.

As shown in FIG. 7B, from the comprehensive feature vector 770 for improved clustering: the user is represented by combined data features from multiple sources and institutions (e.g., height 711, average steps per day 721, number of misdemeanors 741, hours online 751 and income 781. Each data feature can be weighted based on the evaluation domain (e.g., in medical domain, place more weight on medical record data). As previously mentioned, the outlier user data can be removed to improve clustering. The clusters based on the feature data are shown as cluster 790 and cluster 791 (with a cluster of users 792).

Figure 8:
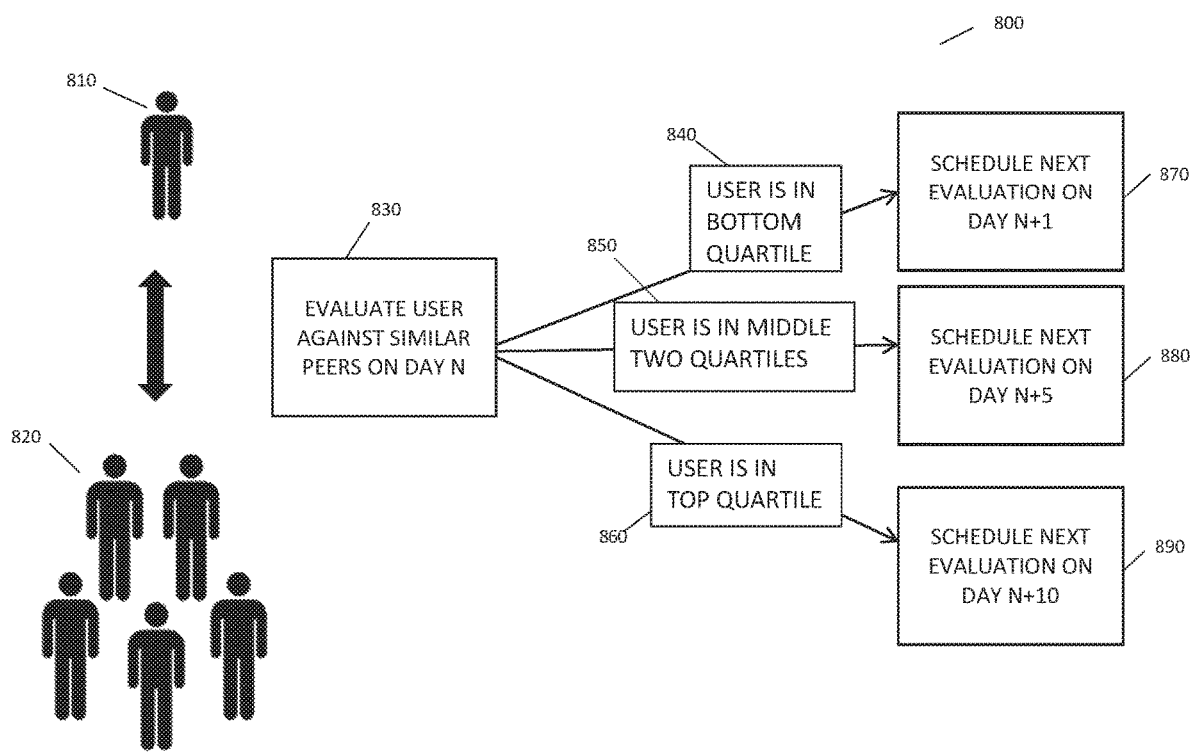
FIG. 8 shows adaptive evaluation frequency for automatically performing user evaluations in view of similar peer groups based on multiple connected devices and multiple institutions, according to an embodiment.

FIG. 8 shows an example 800 for adaptive evaluation frequency for automatically performing user evaluations in view of similar peer groups based on multiple connected devices and multiple institutions, according to an embodiment. In one or more embodiments, the frequency of the evaluations dynamically changes based on context and prior evaluation results. the real-time evaluation engine 250 generates the user's assessment at a frequency that can dynamically change and is adaptive to the user's context. In one embodiment, a user 810 is evaluated against similar peers 820 on day N at block 830, where N is a positive integer. According to the evaluation, if the user 810 evaluates in the bottom quartile at block 840, the next evaluation is scheduled on day N+1 in block 870. If the user 810 evaluates in the middle two quartiles at block 850, the next evaluation is scheduled on day N+5 in block 880. If the user 810 evaluates in the top quartile at block 860, the next evaluation is scheduled on day N+10 in block 890. In other examples, the additional number of days may be selected as necessary for the application.

In one or more embodiments, the frequency of evaluations may be proportional to the importance of the evaluation to the user's well-being. For example, the assessment is generated more frequently if the user is at risk and is not making progress. In a health context, if a physician instructs the user to walk 20,000 steps per day and the user is consistently within the bottom 10 percent of his or her peer group based on prior evaluation results, then the real-time evaluation engine 250 increases the frequency of the evaluations.

In one or more embodiments, the real-time evaluation engine 250 executes an evaluation as soon as the group's data or the user's data is updated or is made available. In another embodiment, when any user's data is updated and made available to the REST API server(s) 461 (FIG. 4), a database trigger runs to initiate the computation of the descriptive statistics and the placement of each user within the context of those descriptive statistics. The user's data and placement within the peer group can further be recorded as part of a time series that is reviewable immediately and at a later time.

Figure 9:
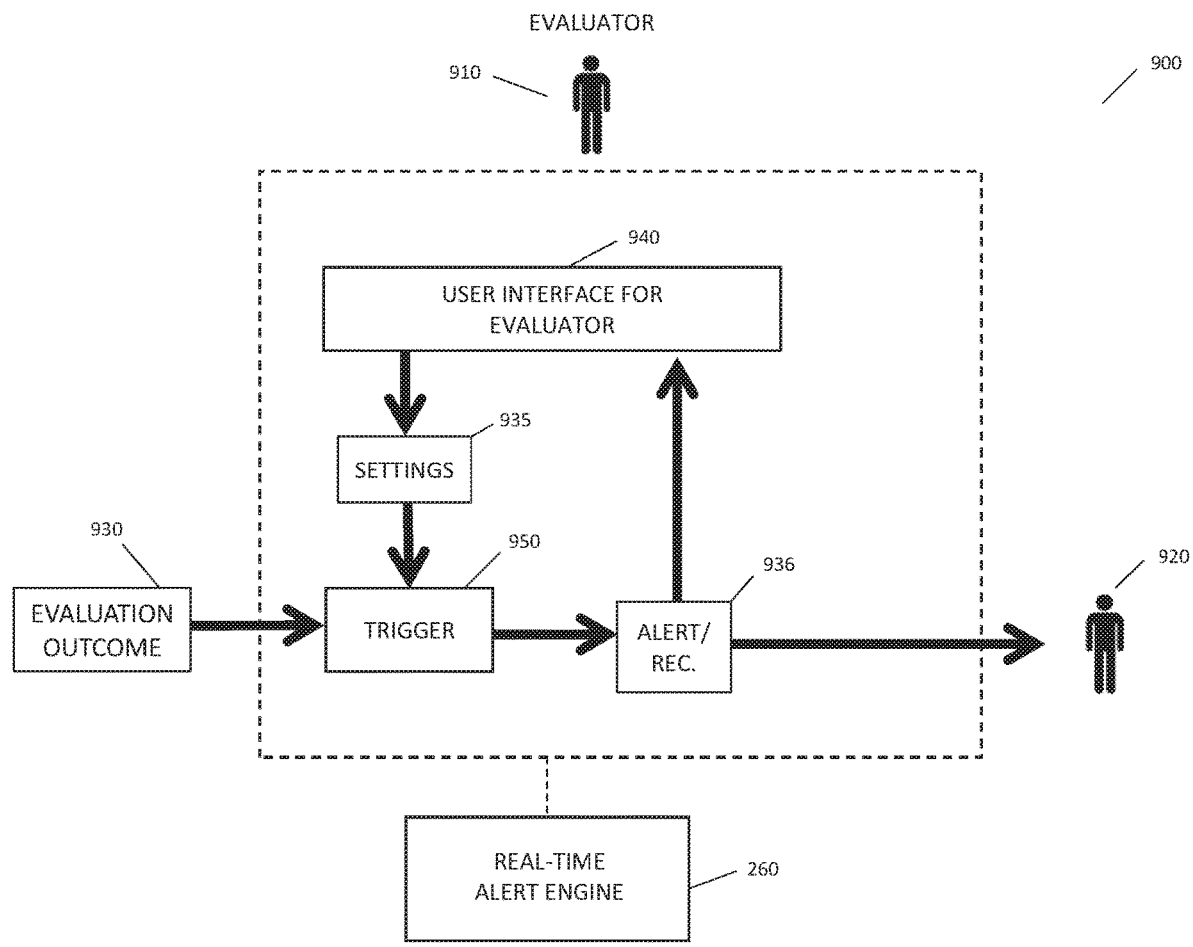
FIG. 9 shows real-time alerts and recommendations for automatically performing user evaluations in view of similar peer groups based on multiple connected devices and multiple institutions, according to an embodiment.

FIG. 9 shows an example 900 for real-time alerts and recommendations 936 for automatically performing user evaluations in view of similar peer groups based on multiple connected devices and multiple institutions, according to an embodiment. In one or more embodiments, an alert and recommended course of action is automatically generated for poor performance. The example 900 begins with an evaluation outcome 930 generated by the real-time evaluation engine 250. In one or more embodiments, the evaluator 910 selects preference settings 935 for alerts or recommendations 936 from the user interface for evaluator 940 (e.g., from a computing device, a smart phone or smart device, a tablet, etc.) for triggering 950 an alert and/or recommendation 936. The real-time alert engine 260 determines when to cause a trigger 950 to initiate an alert and/or recommendation 936 to be sent to the electronic device of a user 920.

In one or more embodiments, if a user is performing poorly with respect to one or more of the assessment metrics, then the real-time alert engine generates an alert and a recommended course of action to address the issue. Such a recommendation can be directly actionable (that is, the user can perform some tangible action in response to the alert and/or recommendation 936) if the assessment metric responds directly to the user's action. For example, in one or more embodiments if a medical patient's average daily exercise duration falls below the first quartile within the peer group, an alert 936 will be generated and emailed to the user 920 with the recommendation 936 resolution being for the user to increase the daily exercise duration. Here, the real-time alert engine 260 generates a recommendation 936 for increased exercise; the user's subsequent action of increased exercise can be directly measured by the assessment metric. The assessment can also be delivered to the evaluator 910 in real-time so that he or she can provide encouragement or guidance to help the user 920 improve.

In one or more embodiments, the assessment or evaluation outcome 930 can be used by the evaluator 910 at the time of formal assessment. The descriptive statistics and the user's 920 placement within the peer group may be useful to the evaluator 910 at the time of the formal assessment. The generated time series may help the evaluator 910 determine that the user 920 is making positive progress over time. Further, the real-time alert engine 260 may help the evaluator 910 choose a beneficial course of action. For example, in the medical context, the evaluator 910 may find that an entire peer group is responding positively to a particular medication or treatment and may thus use that procedure with a different peer group. In one or more embodiments, alerts 936 can be triggered by trigger 950 if the real-time alert engine 260 obtains the information that the user 920 is at risk of failing a goal. In one or more embodiments, the recommendations 936 produce actionable items, e.g. sending a message of "Go out and walk more," "Work harder," etc.

Figure 10:
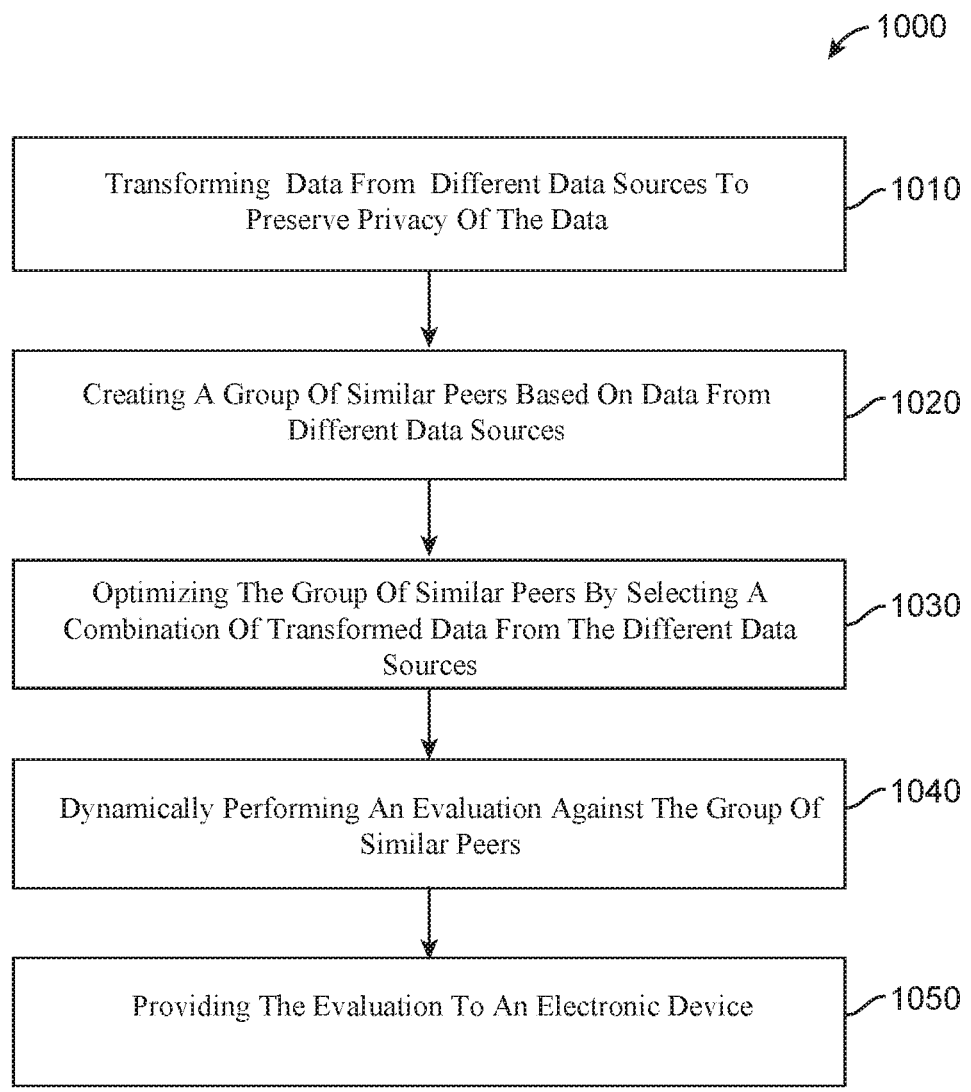
FIG. 10 shows a block diagram for a process for automatically performing user evaluations in view of similar peer groups based on multiple connected devices and multiple institutions, according to an embodiment.

FIG. 10 shows a block diagram for a process 1000 of user evaluations, according to an embodiment. In block 1010 the data from different data sources is transformed to preserve privacy of the data. In block 1020 process 1000 creates the group of similar peers based on data from different data sources (e.g., external data sources 220 (FIG. 2) from multiple institutions and multiple connected devices). In block 1030, the group of similar peers is optimized by selecting a combination of transformed data from the different data sources. In block 1040 an evaluation for a user against the group of similar peers is dynamically performed (e.g., by the real-time evaluation engine 250) based on evaluation metrics. In block 1050 the evaluation is provided to an electronic device.

In one or more embodiments, process 1000 may provide that the frequency of the evaluation is dynamically adaptable and is based on context and a result of the evaluation. Process 1000 may provide that the group of similar peers is determined by applying clustering to find clusters for closest peers according to distance as measured with data obtained from the multiple institutions. Process 1000 may provide that each institution maintains its own private raw data, and that transforming includes converting the private raw data to unidentifiable numeric features.

Process 1000 may further provide that users in a same cluster are measured according to the evaluation metrics, and a particular user is assessed according to placement with respect to descriptive statistics for an entire group. In one or more embodiments, process 1000 may further include generating and sending an alert (e.g., triggered from the real-time alert engine 260, FIG. 2) and a recommended course of action upon determining that a user falls within a particular region (e.g., quartile) of the entire group.

In one or more embodiments, process 1000 may include monitoring additional data and/or different types of data based on a type of evaluation technique. Process 1000 may additionally include customizing data collection based on at least one of type of the electronic device and capability of the electronic device.

Figure 11:
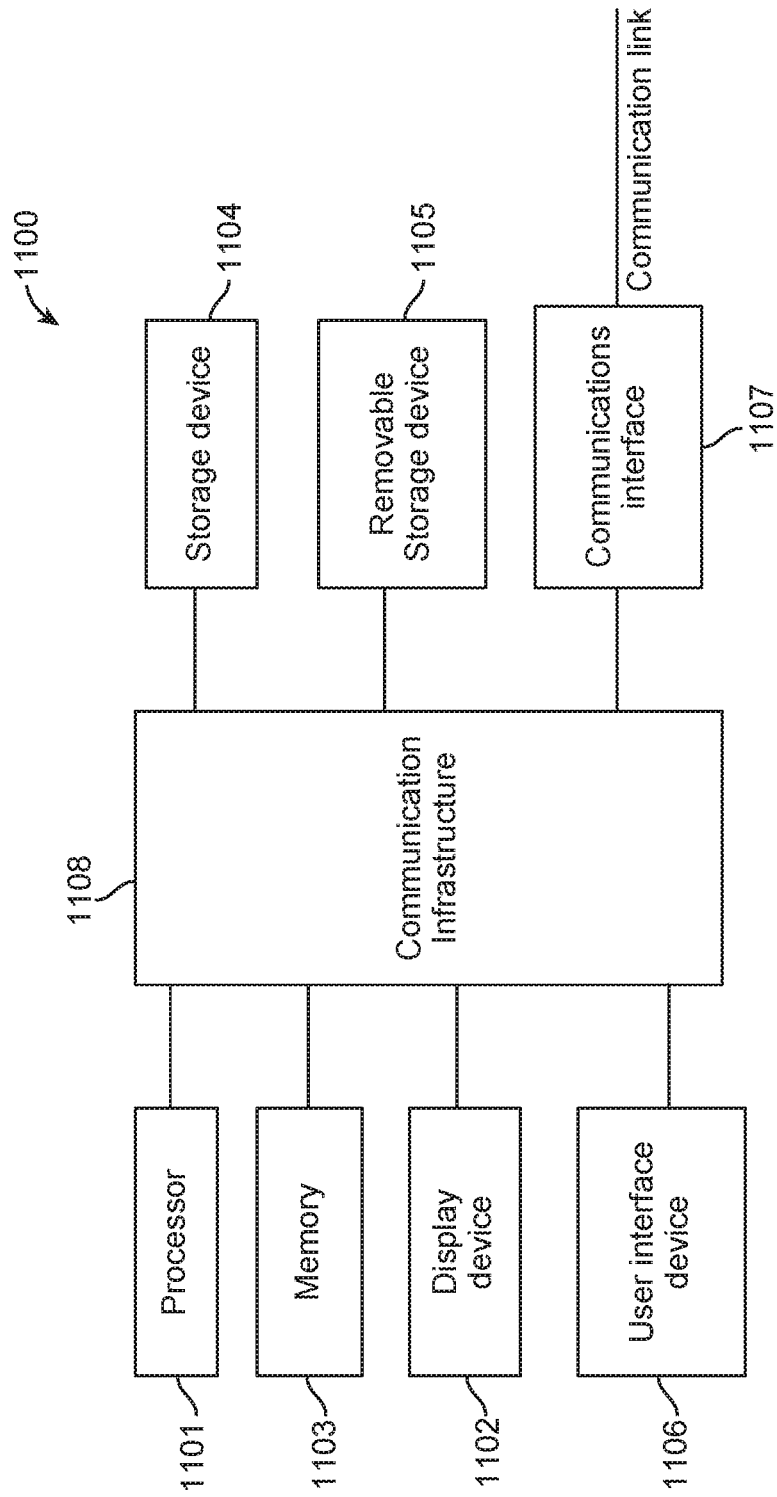
FIG. 11 is an exemplary high-level block diagram showing an information processing system comprising a computer system useful for implementing disclosed embodiments.

FIG. 11 is a high-level block diagram showing an information processing system comprising a computer system 1100 useful for implementing the disclosed embodiments. Computer system 1100 may be incorporated in a device 52, 56, FIG. 1, the cloud platform or server 230 (FIG. 2), or the REST API server(s) 461 (FIG. 4). The computer system 1100 includes one or more processors 1101 (e.g., processor(s) of the components in the cloud platform or server 230, FIG. 2), and can further include an electronic display device 1102 (for displaying video, graphics, text, and other data), a main memory 1103 (e.g., random access memory (RAM)), storage device 1104 (e.g., hard disk drive), removable storage device 1105 (e.g., removable storage drive, removable memory device, a magnetic tape drive, optical disk drive, computer readable medium having stored therein computer software and/or data), user interface device 1106 (e.g., keyboard, touch screen, keypad, pointing device), and a communication interface 1107 (e.g., modem, a network interface (such as an Ethernet card), a communications port, or a PCMCIA slot and card). The communication interface 1107 allows software and data to be transferred between the computer system and external devices (e.g., over communication path 54, FIG. 1). The system 1100 further includes a communications infrastructure 1108 (e.g., a communications bus, cross-over bar, or network) to which the aforementioned devices/processors 1101 through 1107 are connected.

Information transferred via communications interface 1107 may be in the form of signals such as electronic, electromagnetic, optical, or other signals capable of being received by communications interface 1107, via a communication link that carries signals and may be implemented using wire or cable, fiber optics, a phone line, a cellular phone link, a radio frequency (RF) link, and/or other communication channels. Computer program instructions representing the block diagram and/or flowcharts herein may be loaded onto a computer, programmable data processing apparatus, or processing devices to cause a series of operations performed thereon to produce a computer implemented process. In some embodiments, processing instructions for flowchart 300 (FIG. 3), example 400 (FIG. 4), example 500 (FIG. 5), example 600 (FIG. 6), example 800 (FIG. 8), example 900 (FIG. 9) and processing instructions for process 1000 (FIG. 10) may be stored as program instructions on the memory 1103, storage device 1104 and the removable storage device 1105 for execution by the processor 1101.

Embodiments have been described with reference to flowchart illustrations and/or block diagrams of methods, apparatus (systems) and computer program products. Each block of such illustrations/diagrams, or combinations thereof, can be implemented by computer program instructions. The computer program instructions when provided to a processor produce a machine, such that the instructions, which execute via the processor create means for implementing the functions/operations specified in the flowchart and/or block diagram. Each block in the flowchart/block diagrams may represent a hardware and/or software processor/process or logic. In alternative implementations, the functions noted in the blocks may occur out of the order noted in the figures, concurrently, etc.

The terms "computer program medium," "computer usable medium," "computer readable medium", and "computer program product," are used to generally refer to media such as main memory, secondary memory, removable storage drive, a hard disk installed in hard disk drive, and signals. These computer program products are means for providing software to the computer system. The computer readable medium allows the computer system to read data, instructions, messages or message packets, and other computer readable information from the computer readable medium. The computer readable medium, for example, may include non-volatile memory, such as a floppy disk, ROM, flash memory, disk drive memory, a CD-ROM, and other permanent storage. It is useful, for example, for transporting information, such as data and computer instructions, between computer systems. Computer program instructions may be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

As will be appreciated by one skilled in the art, aspects of the embodiments may be embodied as a system, method or computer program product. Accordingly, aspects of the embodiments may take the form of an entirely hardware embodiment, an entirely software embodiment (including firmware, resident software, micro-code, etc.) or an embodiment combining software and hardware aspects that may all generally be referred to herein as a "circuit," "processor" or "system." Furthermore, aspects of the embodiments may take the form of a computer program product embodied in one or more computer readable medium(s) having computer readable program code embodied thereon.

Any combination of one or more computer readable medium(s) may be utilized. The computer readable medium may be a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Computer program code for carrying out operations for aspects of one or more embodiments may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of one or more embodiments are described above with reference to flowchart illustrations and/or block diagrams of methods, apparatus (systems) and computer program products. It will be understood that each block of the flowchart illustrations and/or block diagrams, and combinations of blocks in the flowchart illustrations and/or block diagrams, can be implemented by computer program instructions. These computer program instructions may be provided to a special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods, and computer program products according to various embodiments. In this regard, each block in the flowchart or block diagrams may represent a process, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

References in the claims to an element in the singular is not intended to mean "one and only" unless explicitly so stated, but rather "one or more." All structural and functional equivalents to the elements of the above-described exemplary embodiments that are currently known or later come to be known to those of ordinary skill in the art are intended to be encompassed by the present claims. No claim element herein is to be construed under the provisions of 35 U.S.C. section 112, sixth paragraph, unless the element is expressly recited using the phrase "means for" or "step for."

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the embodiments has been presented for purposes of illustration and description, but is not intended to be exhaustive or limited to the embodiments in the form disclosed. Many modifications and variations will be apparent to those of ordinary skill in the art without departing from the scope and spirit of the invention.

Though the embodiments have been described with reference to certain versions thereof; however, other versions are possible. Therefore, the spirit and scope of the appended claims should not be limited to the description of the preferred versions contained herein.

What is claimed is:

1. A method comprising:
obtaining streaming data from different data sources comprising connected devices and external online data sources, wherein the streaming data from the connected devices comprises data from one or more of real-time sensors, smartphones, wearable devices or industrial devices;
transforming the streaming data from the different data sources to preserve privacy of the data, wherein transformation is applied to a feature vector of each user into a different space and each transformed feature vector keeps a smaller number of features than the feature vector;
creating a group of similar peers based on the streaming data from the different data sources;
optimizing the group of similar peers by selecting a combination of transformed data from the different data sources, wherein the group of similar peers is determined by applying a clustering process to find clusters for closest peers according to distance;
dynamically processing, by at least one hardware processor, one or more cloud-based analyses for the user against the group of similar peers based on evaluation metrics, wherein the one or more cloud-based analyses are processed continuously in a real-time manner;
applying feature weighting to particular data features of the streaming data that are relevant to a particular application domain, wherein each data feature is weighted based on an evaluation domain;
generating, based on performance for the one or more cloud-based analyses, an alert and a recommendation, and a realtime alert engine determines when to cause a trigger to initiate an alert and recommendation to an electronic device; and
transmitting at least one of the alert, the recommendation or an evaluation to the electronic device.

2. The method of claim 1, wherein processing frequency of the one or more cloud-based analyses is dynamically adaptable and is based on context and evaluation results.

3. The method of claim 1, wherein:
each institution of the plurality of institutions maintains its own private raw data; and
transforming comprises converting the private raw data to unidentifiable numeric features.

4. The method of claim 1, wherein users in a same cluster are measured according to the evaluation metrics, and a particular user is assessed according to placement with respect to descriptive statistics for an entire group.

5. The method of claim 1, wherein the recommendation comprises a recommended course of action that is determined depending on a user placement within a particular region of the entire group.

6. The method of claim 1, further comprising:
monitoring at least one of additional data and different types of data based on a type of evaluation technique.

7. The method of claim 1, further comprising:
customizing data collection based on at least one of type of the electronic device and capability of the electronic device.

8. An electronic device comprising:
a memory configured to store instructions;
at least one processor configured to execute the instructions to:
obtain streaming data from different data sources comprising connected devices and external online data sources, wherein the streaming data from the connected devices comprises data from one or more of real-time sensors, smartphones, wearable devices or industrial devices;
transform the streaming data from the different data sources to preserve privacy of the data, wherein transformation is applied to a feature vector of each user into a different space and each transformed feature vector keeps a smaller number of features than the feature vector;
create a group of similar peers based on the streaming data from the different data sources;
optimize the group of similar peers by selection of a combination of transformed data from the different data sources, wherein the group of similar peers is determined by applying a clustering process to find clusters for closest peers according to distance;

dynamically process one or more cloud-based analyses for the user against the group of similar peers based on evaluation metrics, wherein the one or more cloud-based analyses are processed continuously in a real-time manner;

apply feature weighting to particular data features of the streaming data that are relevant to a particular application domain, wherein each data feature is weighted based on an evaluation domain;

generate, based on performance for the one or more cloud-based analyses, an alert and a recommendation, and a realtime alert engine determines when to cause a trigger to initiate an alert and recommendation to the electronic device; and transmit at least one of the alert, the recommendation or an evaluation to a display of the electronic device.

9. The electronic device of claim 8, wherein processing frequency of the one or more cloud-based analyses is dynamically adaptable and is based on context and evaluation results.

10. The electronic device of claim 8, wherein:
each institution of the plurality of institutions maintains its own private raw data; and
data is transformed based on conversion of the private raw data to unidentifiable numeric features.

11. The electronic device of claim 10, wherein users in a same cluster are measured according to the evaluation metrics, and a particular user is assessed according to placement with respect to descriptive statistics for an entire group.

12. The electronic device of claim 8, wherein the recommendation comprises a recommended course of action that is determined depending on a user placement-within a particular region of the entire group.

13. The electronic device of claim 8, wherein the at least one processor is further configured to execute the instructions to:
monitor at least one of additional data and different types of data based on a type of evaluation technique; and
customize data collection based on at least one of type of the electronic device and capability of the electronic device.

14. A non-transitory processor-readable medium that includes a program that when executed by a processor performs a method comprising:
obtaining streaming data from different data sources comprising connected devices and external online data sources, wherein the streaming data from the connected devices comprises data from one or more of real-time sensors, smartphones, wearable devices or industrial devices;
transforming the streaming data from the different data sources to preserve privacy of the data, wherein transformation is applied to a feature vector of each user into a different space and each transformed feature vector keeps a smaller number of features than the feature vector;
creating, by the processor, a group of similar peers based on the streaming data from the different data sources;
optimizing the group of similar peers by selecting a combination of transformed data from the different data sources to optimize, wherein the group of similar peers is determined by applying a clustering process to find clusters for closest peers according to distance;
dynamically processing, by at least one hardware processor, one or more cloud-based analysis for the user against the group of similar peers based on evaluation metrics, wherein the one or more cloud-based analyses are processed continuously in a real-time manner;
applying feature weighting to particular data features of the streaming data that are relevant to a particular application domain, wherein each data feature is weighted based on an evaluation domain;
generating, based on performance for the one or more cloud-based analyses, an alert and a recommendation, and a realtime alert engine determines when to cause a trigger to initiate an alert and recommendation to an electronic device; and
transmitting at least one of the alert, the recommendation or an evaluation to the electronic device.

15. The non-transitory processor-readable medium of claim 14, wherein:
processing frequency of the one or more cloud-based analyses is dynamically adaptable and is based on context and evaluation results.

16. The non-transitory processor-readable medium of claim 15, wherein:
each institution of the plurality of institutions maintains its own private raw data, and transforming comprises converting the private raw data to unidentifiable numeric features;
users in a same cluster are measured according to the evaluation metrics; and
a particular user is assessed according to placement with respect to descriptive statistics for an entire group.

17. The non-transitory processor-readable medium of claim 14, wherein the recommendation comprises a recommended course of action that is determined depending on a user placement within a particular region of the entire group.

18. The non-transitory processor-readable medium of claim 14, wherein the method further comprises:
monitoring at least one of additional data and different types of data based on a type of evaluation technique; and
customizing data collection based on at least one of type of the electronic device and capability of the electronic device.

* * * * *